United States Patent

Barlow et al.

Patent Number: 4,550,111
Date of Patent: Oct. 29, 1985

[54] ALKANOLAMINE DERIVATIVES

[75] Inventors: Jeffrey J. Barlow, Stockport; Leslie H. Smith, Cheadle, both of England

[73] Assignee: Imperial Chemical Industries plc, London, England

[21] Appl. No.: 459,142

[22] Filed: Jan. 19, 1983

[30] Foreign Application Priority Data

Jan. 29, 1982 [GB] United Kingdom ............... 8202596

[51] Int. Cl.$^4$ ................. C07D 237/12; C07D 237/20; A61K 31/495
[52] U.S. Cl. ..................................... 514/255; 544/407
[58] Field of Search ........................ 544/407; 514/255

[56] References Cited

U.S. PATENT DOCUMENTS

| | | | |
|---|---|---|---|
| 3,544,568 | 12/1970 | Cragoe et al. | 544/407 |
| 3,577,418 | 5/1971 | Cragoe et al. | 544/407 |
| 3,655,663 | 4/1972 | Wasson | 544/134 |
| 4,034,106 | 7/1977 | Smith | 424/322 |
| 4,115,409 | 9/1978 | Large et al. | 544/35 |
| 4,115,575 | 9/1978 | Frei et al. | 544/408 |
| 4,139,623 | 2/1979 | Jaeggi et al. | 544/408 |
| 4,211,878 | 7/1980 | Smith | 424/275 |
| 4,219,561 | 8/1980 | Smith | 424/275 |
| 4,221,807 | 9/1980 | Smith | 424/278 |
| 4,399,138 | 8/1983 | Barlow et al. | 544/407 |

Primary Examiner—Donald G. Daus
Assistant Examiner—William A. Teoli, Jr.
Attorney, Agent, or Firm—Cushman, Darby & Cushman

[57] ABSTRACT

Alkanolamine derivatives of the formula

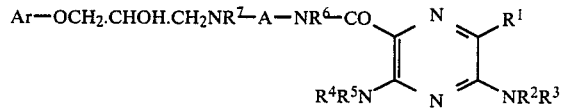

wherein Ar is phenyl or napthyl which is unsubstituted or which bears one or two defined substituents, or Ar is certain defined heterocyclic or bicyclic aromatic systems;

wherein $R^1$ is halogen, cyano, trifluoromethyl or trifluoromethylthio;

wherein either $R^2$ and $R^3$ each is hydrogen or alkyl, or $R^2$ is hydrogen and $R^3$ is cycloalkyl or cycloalkyl-alkyl, or $R^2$ and $R^3$ are joined to form, together with the adjacent nitrogen atom, a heterocyclic group;

wherein either $R^4$ is hydrogen and $R^5$ is hydrogen or alkyl, or $R^4$ is hydrogen and $R^5$ and $R^6$ are joined together to form alkylene, or $R^4$, $R^5$ and $R^6$ are joined together to form alk-1-yl-ω-ylidene;

wherein either $R^6$ and $R^7$ each is hydrogen or alkyl, or $R^6$ is joined to $R^4$ or to $R^4$ and $R^5$ as defined above and $R^7$ is hydrogen or alkyl, or $R^6$ and $R^7$ are joined together to form alkylene, or one of $R^6$ and $R^7$ is hydrogen or alkyl and the other of $R^6$ and $R^7$ is joined to A as defined below;

and wherein either A is alkylene, cycloalkylene or cycloalkylene-alkylene, or A together with either $R^6$ and its accompanying nitrogen atom, or $R^7$ and its accompanying nitrogen atom, form pyrrolidine-diyl or piperidine-diyl;

and acid-addition salts thereof; processes for their manufacture and pharmaceutical compositions containing them. The compounds possess β-adrenergic blocking and/or diuretic activity.

9 Claims, No Drawings

ALKANOLAMINE DERIVATIVES

This invention relates to new alkanolamine derivatives some of which possess β-adrenergic blocking activity, some of which possess diuretic activity and some of which possess both said activities.

According to the invention there is provided an alkanolamine derivative of the formula

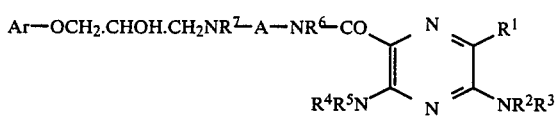

wherein Ar is phenyl or naphthyl which is unsubstituted or which bears one or two substituents selected from halogen, trifluoromethyl, hydroxy, amino, nitro, carbamoyl and cyano, and alkyl, alkenyl, alkoxy, alkenyloxy, alkylthio, alkanoyl, carbamoylalkyl and alkanoylamino each of up to 6 carbon atoms, or Ar is 2-methyl-4-indolyl, 2-oxo-1,2,3,4-tetrahydro-5-quinolyl, 4-indolyl, 4-carbazolyl, 4-benzo[b]thienyl, 5-benzo[1,4]-dioxanyl, 4- or 5-indanyl, 5- or 6-(1,2,3,4-tetrahydronaphthyl), 2,3-dihydroxy-1,2,3,4-tetrahydronaphth-5-yl or 4-morpholino-1,2,5-thiadiazol-3-yl; wherein $R^1$ is halogen, cyano, trifluoromethyl or trifluoromethylthio;
wherein either $R^2$ and $R^3$, which may be the same or different, each is hydrogen or alkyl of up to 6 carbon atoms; or $R^2$ is hydrogen and $R^3$ is cycloalkyl of 3 to 6 carbon atoms or cycloalkyl-alkyl wherein cycloalkyl is of 3 to 6 carbon atoms and alkyl is of up to 6 carbon atoms; or $R^2$ and $R^3$ are joined to form, together with the adjacent nitrogen atom, a 5- or 6-membered fully saturated heterocyclic group which may contain an additional nitrogen, oxygen or sulphur heteroatom;
wherein either $R^4$ is hydrogen and $R^5$ is hydrogen or alkyl of up to 6 carbon atoms; or $R^4$ is hydrogen and $R^5$ and $R^6$ are joined together to form alkylene of 1 or 2 carbon atoms; or $R^4$, $R^5$ and $R^6$ are joined together to form alk-1-yl-ω-ylidene of 1 or 2 carbon atoms;
wherein either $R^6$ and $R^7$, which may be the same or different, each is hydrogen or alkyl of up to 6 carbon atoms; or $R^6$ is joined to $R^4$ or to $R^4$ and $R^5$ as defined above and $R^7$ is hydrogen or alkyl of up to 6 carbon atoms; or $R^6$ and $R^7$ are joined together to form alkylene of 1 or 2 carbon atoms; or one of $R^6$ and $R^7$ is hydrogen or alkyl of up to 6 carbon atoms and the other of $R^6$ and $R^7$ is joined to A as defined below;
and wherein either A is alkylene of 2 to 6 carbon atoms, or cycloalkylene of 3 to 6 carbon atoms, or cycloalkylenealkylene of 4 to 7 carbon atoms, or wherein A together with either $R^6$ and its accompanying nitrogen atom, or $R^7$ and its accompanying nitrogen atom, form pyrrolidinediyl or piperidine-diyl;
or an acid-addition salt thereof.

It will be observed that the alkanolamine derivative of the invention possesses at least one asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically active form which possesses either β-adrenergic blocking activity or diuretic activity, it being a matter of common general knowledge how a racemic compound may be resolved into optically-active forms, and how the β-adrenergic blocking or diuretic activity of these forms may be determined. It is further to be understood that β-adrenergic blocking activity usually predominates in that optically-active form which has the "S" absolute configuration of the said —CHOH— group.

A suitable value for the one or two substituents in Ar when it is phenyl or naphthyl is, for example, one or two substituents selected from fluoro, chloro, bromo, iodo, trifluoromethyl, hydroxy, amino, nitro, carbamoyl, cyano, methyl, ethyl, n-propyl, t-butyl, allyl, methoxy, isopropoxy, allyloxy, methylthio, formyl, acetyl, acetamido and carbamoylmethyl substituents.

A suitable value for $R^1$ when it is halogen is fluoro, chloro, bromo or iodo. $R^1$ is preferably chloro.

A suitable value for $R^2$, $R^3$, $R^5$, $R^6$ or $R^7$ when it is alkyl is, for example, methyl, ethyl or isopropyl.

A suitable value for $R^3$ when it is cycloalkyl or cycloalkyl-alkyl is, for example, cyclopentyl, cyclohexyl or cyclopropylmethy.

A suitable heterocyclic group formed by $R^2$, $R^3$ and the adjacent nitrogen atom is, for example, pyrrolidino, piperidino, morpholino, thiamorpholino, piperazino or 4-methylpiperazino.

The alkylene group formed by $R^5$ and $R^6$ joined together may be methylene, ethylene or ethylidene

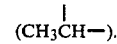

$(CH_3\overset{|}{C}H—)$.

The alk-1-yl-ω-ylidene group formed by $R^4$, $R^5$ and $R^6$ joined together is preferably methine (—CH=).

The alkylene group formed by $R^6$ and $R^7$ is preferably ethylene, and when this group is present A is preferably also ethylene so that —$NR^7$—A—$NR^6$— is piperazine-1,4-diyl.

A suitable value for A when it is alkylene is, for example, ethylene, trimethylene, tetramethylene, hexamethylene, 1-methylethylene (—CHMe—CH$_2$), 1,1-dimethylethylene, (—CMe$_2$—CH$_2$—), 2-methylethylene (—CH$_2$—CHMe—) or 2,2-dimethylethylene (—CH$_2$—CMe$_2$—).

A suitable value for A when it is cycloalkylene is, for example, cyclohex-1,2-diyl, cyclohex-1,3-diyl, cyclohex-1,4-diyl, cyclopent-1,2-diyl, cyclobut-1,2-diyl or cycloprop-1,2-diyl.

A suitable value for A when it is cycloalkylenealkylene is, for example, a group of the formula —$CR^{11}R^{12}$—CH$_2$ wherein $R^{11}$ and $R^{12}$ are joined to form alkylene of 2 to 5 carbon atoms, that is, cycloprop-1-yl-1-methyl, cyclobut-1-yl-1-methyl, cyclopent-1-yl-1-methyl or cyclohex-1-yl-1-methyl.

A preferred value for the group formed by A and —$NR^6$— or —$NR^7$— is piperidine-1,4-diyl such that the group —$NR^7$—A—$NR^6$— is piperidine-1-yl-4-amino.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, succinate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

A preferred alkanolamine derivatives of the invention has the formula given above wherein Ar has the meaning stated above, and particularly wherein Ar is α-naphthyl, or phenyl which is unsubstituted or which bears a single substituent in the 2-position which is a fluoro, chloro, nitro, cyano, methyl, ethyl, allyl or methoxy, substituent, wherein $R^1$ is chloro, wherein $R^2$, $R^3$, $R^4$, $R^5$, $R^6$ and $R^7$ are all hydrogen and wherein A is ethylene or 1,1-dimethylethylene, or is an acid-addition salt thereof.

As stated above, an alkanolamine derivative of the invention may possess β-adrenergic blocking activity, or diuretic activity, or both such activities. In general, β-adrenergic blocking activity will be relatively high when A is α-branched-chain alkylene, especially 1,1-dimethylethylene, and when Ar is α-naphthyl or unsubstituted or o-substituted phenyl. β-adrenergic blocking activity may be reduced by choosing a "de-activating" value for Ar, for example β-naphthyl or 3,4-dichlorophenyl. Diuretic activity is relatively high when Ar is α- or β-naphthyl, or phenyl which is unsubstituted or which bears one or two halogen, alkyl, alkenyl or alkoxy substituents, and when A is such that no more than 2 carbon atoms separate the two nitrogen atoms. Diuretic activity may be reduced by choosing, for example, trimethylene or tetramethylene for A, or cyano or carbamoyl as substituents in Ar. It is clear therefore by appropriate selection of values for the various substituents in Ar, or the value of A, the balance between diuretic and β-adrenergic blocking activity may be varied as desired.

Specific alkanolamine derivatives of the invention are hereinafter described in the Examples. Of these, preferred compounds which combine both β-adrenergic blocking activity and diuretic activity are N-β-(2-hydroxy-3-α-naphthyloxypropylamino)ethyl(3,5-diamino-6-chloropyrazine-2-carbox)amide and the corresponding 2-hydroxy-3-phenoxypropylamino and 2-hydroxy-3-o-fluorophenoxypropylamino analogues, and N-[2-methyl-2-(2-hydroxy-3-o-tolyloxypropylamino)propyl](3,5-diamino-6-chloropyrazine-2-carbox)amide, and the acid-addition salts thereof.

The alkanolamine derivative of the invention may be manufactured by any chemical process known to be useful for the manufacture of chemically-analogous compounds.

A preferred process for the manufacture of an alkanolamine derivative of the invention comprises the reaction of a compound of the formula:

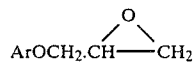

wherein Ar has the meaning stated above, with a compound of the formula

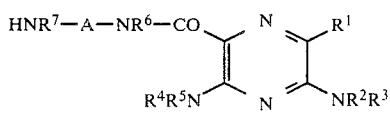

wherein $R^1$, $R^2$, $R^3$, $R^4$, $R^5$, $R^6$, $R^7$ and A have the meanings stated above.

The reaction is conveniently carried out in a diluent or solvent, for example isopropanol, at an elevated temperature for example at the boiling point of the diluent or solvent.

Alternatively, the alkanolamine derivative of the invention may be obtained by the reaction of a compound of the formula:

wherein Ar, $R^6$, $R^7$, and A have the meanings stated above, with a compound of the formula:

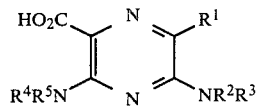

wherein $R^1$, $R^2$, $R^3$, $R^4$ and $R^5$ have the meanings stated above, or with a reactive derivative thereof.

A suitable reactive derivative is, for example, a lower alkyl ester, for example the methyl or ethyl ester. When the acid itself is used as starting material the reaction is preferably carried out in the presence of a condensing agent, for example a carbodiimide.

Optically-active enantiomorphs of the alkanolamine derivative of the invention may be obtained by the resolution by conventional means of the corresponding racemic alkanolamine derivative of the invention.

The alkanolamine derivative in free base form may be converted into an acid-addition salt thereof by reaction with an acid by conventional means.

As stated above, the alkanolamine derivative of the invention or an acid-addition salt thereof possesses either β-adrenergic blocking activity or diuretic activity or both such activities. The β-adrenergic blocking activity may be determined by the effect of the compound in reversing isoprenaline-induced tachycardia in rats or cats, a standard test for the determination of β-adrenergic blocking activity. The diuretic activity may be determined by the effect of the compound in increasing urine volume in rats, a standard test for the determination of diuretic activity. At doses of an alkanolamine derivative of the invention which produce effective β-adrenergic blockade or diuretic activity in rats or cats, no symptoms of toxicity are apparent.

Many β-adrenergic blocking agents, and many diuretic agents, are known, and it is also known to prepare a pharmaceutical composition containing both kinds of drug. For example, compositions containing atenolol and chlorthalidone, or propranolol and bendrofluazide, are commercially available. However, no single chemical compound which possessed both activities to a significant extent was hitherto available.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain in addition to the alkanolamine derivative of the invention, one or more drugs selected from sedatives, for example phenobarbitone, meprobamate, chloropromazine and the benzodiazepine sedative drugs, for example chlordiazepoxide and diazepam; vasodilators, for example glyceryl trinitrate, pentaerythritol tetranitrate, isosorbide dinitrate and hydralazine; other diuretics, for example chlorthalidone, bendrofluazide, hydrochlorothiazide and chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; and α-adrenergic blocking agents, for example phentolamine.

When used for the treatment of heart diseases, for example angina pectoris and cardiac arrhythmias, or for the treatment of hypertension or anxiety states in man, it is expected that the alkanolamie derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

N,N'-dicyclohexylcarbodiimide (2.2 g.) was added to a stirred solution of 3,5-diamino-6-chloropyrazine-2-carboxylic acid (1.9 g.) and N-hydroxysuccinimide (1.2 g.) in dimethylformamide (50 ml.) and the mixture was stirred at laboratory temperature for 1 hour. 1-(2-Amino-1,1-dimethylethyl)amino-3-(2-fluorophenoxy)-propan-2-ol (2.8 g.) was added and the mixture was stirred for a further 18 hours at laboratory temperature and then filtered. The filtrate was evaporated to dryness under reduced pressure and the residue was partitioned between n-butanol (200 ml.) and 6% w/v aqueous sodium bicarbonate solution (100 ml.). The butanol phase was separated, washed with water (100 ml.) and evaporated to dryness under reduced pressure and the residue was chromatographed on a silica column (Merck '60', 50 g., column 140 mm long and 32 mm diameter) using 500 ml. of a 19:1 v/v mixture of chloroform and methanol and then 500 ml. of a 9:1 v/v mixture of chloroform and methanol as eluants. The fractions containing a product with an $R_f$ of 0.2 when examined by thin-layer chromatography using the latter solvent system were collected, combined and evaporated to dryness under reduced pressure. A solution of the residue in ethanol (30 ml.) was added to a solution of oxalic acid (0.8 g.) in ethanol (20 ml.). The mixture was evaporated to dryness under reduced pressure and the residue was crystallised from ethanol (20 ml.). There was thus obtained 3,5-diamino-6-chloro-N-[2-methyl-2-(3-o-fluorophenoxy-2-hydroxypropylamino)propyl]pyrazine-2-carboxamide hydrogen oxalate, m.p. 110°–113° C. (with decomposition).

The 1-(2-amino-1,1-dimethylethyl)amino-3-(2-fluorophenoxy)propan-2-ol used as starting material was obtained as follows:

A mixture of 1,2-epoxy-3-(2-fluorophenoxy)propane (9.2 g.), N-(2-amino-2-methylpropyl)-2-methylpropanamide (8.7 g.), isopropanol (100 ml.) and water (2 ml.) was heated under reflux for 16 hours and then evaporated to dryness under reduced pressure. To the residue was added aqueous 6N-hydrochloric acid (100 ml.) and the mixture was heated at 90° C. for 16 hours, cooled, washed twice with diethyl ether (50 ml. each time), cooled to 0° C. and basified to pH 11 with aqueous 10N-sodium hydroxide solution. The mixture was extracted twice with diethyl ether (200 ml. each time) and the combined extracts were washed with saturated aqueous sodium chloride solution (100 ml.), dried over sodium sulphate and evaporated to dryness. The oily residue consisted of 1-(2-amino-1,1-dimethylethyl)amino-3-(2-fluorophenoxy)propan-2-ol and was used without further purification.

The process described in the first paragraph above was repeated using the appropriate 1-(2-amino-1,1-dimethylethyl)amino-3-aryloxypropan-2-ol (prepared by a similar process to that described in the second paragraph above) as starting material, and there were thus obtained the compounds described in the following table, both of which were crystallized from ethanol:

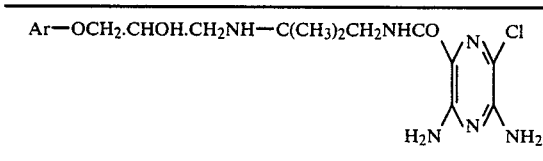

| Ar | Salt | m.p. (°C.) |
| --- | --- | --- |
| 2-tolyl | dihydrochloride | 180–183 (d) |
| 1-naphthyl | hydrogen oxalate | 125–129 |

EXAMPLE 12

The process described in Example 1 was repeated using the appropriate 1-ω-aminoalkylamino-3-aryloxypropan-2-ol as starting material, and there were thus obtained the compounds described in the following table, all of which were hydrogen oxalate salts crystallised from ethanol:

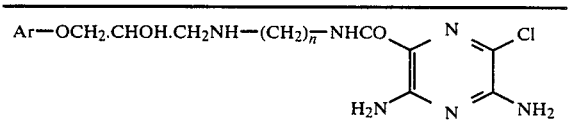

| Ar | n | hydrogen oxalate salt m.p. (°C.) |
| --- | --- | --- |
| 2-cyanophenyl | 2 | 200–203 (d) |
| 2-fluorophenyl | 2 | 208–210 (d) |
| 2-allylphenyl | 2 | 214–215 (d) |
| 2-tolyl | 2 | 221–223 (d) |
| 2-methoxyphenyl | 2 | 205–207 (d) |
| phenyl | 2 | 214–215 (d) |
| 2-ethylphenyl | 2 | 223–224 (d) |
| 2-carbamoylphenyl | 2 | 210–211 (d) |
| 2-naphthyl | 2 | 211–214 (d) |
| 3-fluorophenyl | 2 | 218–220 (d) |
| 2,3-dichlorophenyl | 2 | 226–228 (d) |
| 3,4-dichlorophenyl | 2 | 222–224 (d) |
| 2-nitrophenyl | 2 | 208–209 (d) |
| 2-t-butylphenyl | 2 | 210–211 (d) |
| 4-benzo[b]thienyl | 2 | 232–233 (d) |
| 4-fluorophenyl | 2 | 212–214 (d) |
| 2-fluorophenyl | 3 | 210–212 (d) |
| 1-naphthyl | 3 | 210–212 (d) |
| 1-naphthyl | 4 | 185–193 (d) |

EXAMPLE 3

A mixture of 1,2-epoxy-3-phenoxypropane (1.5 g.), 3,5-diamino-6-chloro-N-(2-amino-2-methylpropyl)-pyrazine-2-carboxamide (2.6 g.) and isopropanol (20 ml.) was heated under reflux for 4 hours and then filtered, and the filtrate was evaporated to dryness under reduced pressure. A solution of the residue in ethanol (50 ml.) was added to a solution of oxalic acid (1.4 g.) in ethanol (50 ml.) and the mixture was filtered. The solid residue was crystallised from ethanol (250 ml.) and there was thus obtained 3,5-diamino-6-chloro-N-[2-methyl-2-(2-hydroxy-3-phenoxypropylamino)propyl]-pyrazine-2-carboxamide oxalate, m.p. 168°–170° C. with decomposition.

The process described above was repeated using the appropriate 2,3-epoxy-1-aryloxypropane as starting material, and there were thus obtained the compounds, of the formula stated in Example 1, described in the following table, all of which were crystallised from ethanol.

| Ar | Salt | m.p. (°C.) |
| --- | --- | --- |
| 2-allylphenyl | hydrogen oxalate | 167–169 |
| 2-chlorophenyl | hydrogen oxalate | 116–119 |
| 2-ethylphenyl | hydrogen oxalate | 175 |
| 2-cyanophenyl | hydrogen oxalate | 156–158 |
| 2-naphthyl | hydrogen oxalate | 179–180 (d) |

The 3,5-diamino-6-chloro-N-(2-amino-2-methylpropyl)pyrazine-2-carboxamide used as starting material was obtained as follows:

A mixture of methyl 3,5-diamino-6-chloropyrazine-2-carboxylate (4.0 g.) and 2-amino-2-methylpropylamine (8.8 g.) was heated at 90° C. under an inert atmosphere for 18 hours, and the excess of diamine was removed by evaporation at 40° C./1.0 mm/Hg. The residue was crystallized from ethanol and there was thus obtained 3,5-diamino-6-chloro-N-(2-amino-2-methylpropyl)-pyrazine-2-carboxamide, m.p. 197°–200° C.

EXAMPLE 4

A mixture of 1-$\beta$-aminoethylamino-3-$\alpha$-naphthoxypropan-2-ol (3.9 g.) and methyl 3,5-diamino-6-chloropyrazine-2-carboxylate (1.1 g.) was heated at 90° C. for 25 hours, cooled and chromatographed on a silica column (Merck '60', 50 g., column 140 mm.long and 32 mm.diameter) using a 9:1 v/v mixture of chloroform and methanol as eluant. The fractions containing a product with an $R_f$ of 0.2 when examined by thin layer chromatography using the above solvent system were collected, combined and evaporated to dryness under reduced pressure. The residue was converted into a hydrogen oxalate salt by a similar procedure to that described in Example 1, and the salt was crystallised from ethanol. There was thus obtained 3,5-diamino-6-chloro-N-$\beta$-(2-hydroxy-3-$\alpha$-naphthoxypropylamino)ethylpyrazine-2-carboxamide hydrogen oxalate, m.p. 224°–226° C. (with decomposition)

The process described above was repeated except that 1-$\beta$-aminoethylamino-3-o-chlorophenoxypropan-2-ol was used as starting material in place of the $\alpha$-naphthoxy analogue, and that the chromatography and salt formation steps were omitted. The crude product was stirred with ethyl acetate, the mixture was filtered and the solid residue was crystallized from ethanol. There was thus obtained 3,5-diamino-6-chloro-N-$\beta$-(3-o-chlorophenoxy-2-hydroxypropylamino)ethylpyrazine-2-carboxamide, m.p. 158°–160° C.

EXAMPLE 5

A mixture of 1-$\beta$-aminoethylamino-3-(5,6,7,8-tetrahydronaphth-1-yloxy)propan-2-ol (1.45 g.), 3,5-diamino-6-chloropyrazine-2-carboxylic N,N-diphenylcarbamic anhydride (1.9 g.) and tetrahydrofuran (20 ml.) was stirred at laboratory temperature for 18 hours, diluted with tetrahydrofuran (20 ml.) and filtered. The filtrate was evaporated to dryness under reduced pressure, the residue was crystallised from acetonitrile and the solid product was dissolved in ethanol (30 ml.). The solution thus obtained was added to a solution of oxalic acid (0.3 g.) in ethanol (20 ml.), the mixture was filtered and there was thus obtained as solid product 3,5-diamino-6-chloro-N-$\beta$-[2-hydroxy-3-(5,6,7,8-tetrahydronaphth-1-yloxy)propylamino]ethylpyrazine-2-carboxamide hydrogen oxalate, m.p. 218°–220° (with decomposition).

The process described above was repeated using the appropriate 1-$\beta$-aminoethylamino-3-aryloxypropan-2-ol as starting material, and there was thus obtained the hydrogen oxalates (or, in one case, the free base) of the compounds, of the formula stated in Example 2 wherein n is 2, described in the following table:

| Ar | m.p. (°C.) | Crystallisation Solvent |
| --- | --- | --- |
| 2-isopropylphenyl | 219–221 (d) | ethanol |
| 2-allyloxyphenyl | (base) 146–147.5 | ethanol |
| indan-5-yl | 226–228.5 (d) | methanol |
| 5,6,7,8-tetrahydronaphth-2-yl | 219–221.5 (d) | ethanol |

EXAMPLE 6

The filtrate from a filtered mixture of 1-$\beta$-aminoethylamino-3-(4-indanyloxy)propan-2-ol dihydrochloride (1.8 g.), triethylamine (1.2 g.) and dimethylformamide (50 ml.) was added to a stirred solution of 3,5-diamino-6-chloropyrazine-2-carboxylic acid (1.0 g.) in dimethylformamide (50 ml.), 1-hydroxybenzotriazole (1.2 g.) and N,N$^1$-dicyclohexylcarbodiimide (1.1 g.) were successively added and the mixture was stirred at laboratory temperature for 18 hours and then filtered. The filtrate was evaporated to dryness under reduced pressure, the residue was suspended in aqueous 1N-sodium hydroxide solution and the mixture was extracted twice with n-butanol (50 ml.each time). The combined extracts were washed twice with water (25 ml. each time), evaporated to dryness under reduced pressure and the residue was chromatographed on a silica gel column (Merck '60', 30 g., column 100 mm. long×30 mm. diameter) using a 9:1 v/v mixture of methylene chloride and methanol (1 liter) and then a 9:1 v/v mixture of methylene chloride and methanol (500 ml.) as eluants. The fractions containing a product with a $R_f$ of 0.2 when examined by thin-layer chromatography on silica gel plates using the latter solvent system were combined and evaporated to dryness under reduced pressure, and a solution of the residue in ethanol (15 ml.) was added to a solution of oxalic acid (0.4 g.) in ethanol (10 ml.). The mixture was filtered, the solid product was crystallised from methanol and there was thus obtained 3,5-diamino-6-chloro-N-β-[2-hydroxy-3-(indan-4-yloxy)propylamino]ethylpyrazine-2-carboxamide hydrogen oxalate, m.p. 240°–241° C. (with decomposition).

EXAMPLE 7

A solution of 3,5-diamino-6-chloropyrazine-2-carboxylic acid (0.85 g.) and 1,1¹-carbonyldiimidazole (0.85 g.) in dimethylformamide (50 ml.) was stirred at laboratory temperature for 90 minutes, 1-β-aminoethylamino-3-p-carbamoylmethylphenoxypropan-2-ol (1.35 g.) was added and the mixture was stirred for 18 hours and then filtered. The filtrate was poured into ice-water (500 ml.) and the mixture was extracted twice with n-butanol (400 ml. each time). The combined extracts were washed with water, filtered and evaporated to dryness under reduced pressure, and the residue was stirred with ethanol. The mixture was filtered and the solid product was crystallised from ethanol. There was thus obtained 3,5-diamino-6-chloro-N-β-[2-hydroxy-3-p-carbamoylmethylphenoxypropylamino]ethylpyrazine-2-carboxamide, m.p. 162°–165° C.

EXAMPLE 8

The process described in Example 6 was repeated except that 1-[2-amino-(R)-1-methylethylamino]-3-α-naphthoxypropan-(R,S)-2-ol dihydrochloride was used as starting material, and that the final product was converted to a dihydrochloride by addition of ethereal hydrogen chloride to a solution of the free base in isopropanol. There was thus obtained 3,5-diamino-6-chloro-N-{(R)-2-[(R,S)-2-hydroxy-3-α-naphthoxypropylamino]propyl}pyrazine-2-carboxamide dihydrochloride, m.p. 232° C.

The 1-[2-amino-(R)-1-methylethylamino]-3-α-naphthoxypropan-(R,S)-2-ol dihydrochloride used as starting material was obtained as follows:

A mixture of 1,2-epoxy-3-α-naphthoxypropane (55.6 g.), (R)-2-aminopropionamide (D-alanine amide, 22.3 g.) and isopropanol (500 ml.) was heated under reflux for 18 hours, cooled and evaporated to dryness. The residue was dissolved in n-butanol (600 ml.) and the solution was washed three times with water (250 ml. each time), concentrated to 100 ml., left at laboratory temperature for 18 hours and then filtered. There was thus obtained as solid product (R)-2-[(R,S)-2-hydroxy-3-α-naphthoxypropylamino]propionamide, m.p.127°–146° C.

A molar solution of diborane in tetrahydrofuran (273 ml.) was added during 30 minutes to a stirred, ice-cooled suspension of the above propionamide (26.2 g.) in tetrahydrofuran (400 ml.) under an atmosphere of argon, and the mixture was stirred at laboratory temperature for 18 hours and then recooled to 0° C. Further diborane solution (182 ml.) was added during 30 minutes, and the mixture was stirred for a further 30 minutes. Aqueous 2N-hydrochloric acid (250 ml.) was slowly added, and the tetrahydrofuran was removed by evaporation. The residual aqueous solution was made just alkaline with aqueous 30% w/v sodium hydroxide solution and was then extracted twice with n-butanol (600 ml. each time). The combined extracts were washed with water and evaporated to dryness under reduced pressure, and the residue was dissolved in isopropanol (800 ml.). The solution was filtered, aqueous 36% hydrochloric acid (4 ml.) was added and the mixture was concentrated to 500 ml., cooled and filtered. There was thus obtained as solid residue 1-[2-amino-(R)-1-methylethylamino]-3-α-naphthoxypropan-(R,S)-2-ol dihydrochloride, m.p. 184°–187° C., which was used without further purification.

EXAMPLE 9

The process described in Example 8 was repeated except that L-alanine amide was used as initial starting material in place of D-alanine amide. There was thus obtained 3,5-diamino-6-chloro-N-{(S)-2-[(R,S)-2-hydroxy-3-α-naphthoxypropylamino]propyl}pyrazine 2-carboxamide, monohydrochloride m.p. 158°–161° C.

EXAMPLE 10

A mixture of 1,2-epoxy-3-(indol-4-yloxy)propane (0.67 g.), 3,5-diamino-6-chloro-N-(2-aminoethyl)pyrazine-2-carboxamide (1.63 g.) and isopropanol (50 ml.) were refluxed together under nitrogen until thin layer chromatography indicated all of the epoxy compound had reacted (about 3 hours). The solvent was removed by rotary evaporator and the resulting yellow solid was chromatographed on silica gel with a 5:1 mixture of chloroform:methanol to give 1.03 g. of product. This material was dissolved in methanol (110 ml.) with warming and the solution was added to oxalic acid (1 equivalent) in methanol (20 ml.). Upon concentration and cooling of the solution, there was obtained 3,5-diamino-6-chloro-N-2-(2-hydroxy-3-indol-4-yloxypropylamino)ethyl-pyrazine-2-carboxamide oxalate, m.p. 214°–216° C. with decomposition.

The process described above was repeated using the appropriate 2,3-epoxy-1-aryloxypropane as the starting material, and there was thus obtained the compounds, of the formula stated in Example 2 wherein n is 2, described in the following table as hydrogen oxalate salts unless otherwise indicated:

| Ar | Melting point (°C.) |
| --- | --- |
| 4-carbazolyl | 169–172* |
| 4-methoxy-1-naphthyl | 227–229 (d) |
| 7-acetamido-1-naphthyl | 220–226 (d) |
| 8-methyl-1-naphthyl | 222–224 (d) |
| 2-methyl-4-indolyl | 195–198 (d) |
| 2-oxo-1,2,3,4-tetrahydro-5-quinolyl | 230–232 (d) |

*Free Base

The 3,5-diamino-6-chloro-N-(2-aminoethyl)-pyrazine-2-carboxamide used as starting material was obtained by the method described in Example 3 substituting the equivalent amount of ethylene diamine for 2-amino-2-methylpropylamine. The appropriate 2,3-epoxy-1-aryloxypropanes are obtained as set forth in Example 1 of United Kingdom Patent 1,369,580 published 9 October 1974.

EXAMPLE 11

The process described in Example 10 was repeated using 3,5-diamino-6-chloro-N-(2-amino-2-methylpropyl)pyrazine-2-carboxamide in the place of 3,5-diamino-6-chloro-N-(2-aminoethyl)pyrazine-2-carboxamide and the appropriate 2,3-epoxy-1-aryloxypropanes to obtain the compounds, of the formula stated in Example 1, described in the following table as hydrogen oxalate salts unless otherwise indicated:

| Ar | Melting point (°C.) |
| --- | --- |
| 4-methoxy-1-naphthyl | 192–194 (d) |
| 4-carbazolyl | 238–240 (d) |

| Ar | Melting point (°C.) |
|---|---|
| 4-indolyl | 134–137 (d) |
| 8-methyl-1-naphthyl | 178–182 (d) |
| 2-methyl-4-indolyl | 170–176 (d) |
| 2-oxo-1,2,3,4-tetrahydro-5-quinolyl | 185–187* |

*Free Base

What we claim is:

1. A compound of the formula

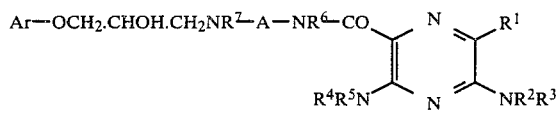

wherein Ar is phenyl or naphthyl which is unsubstituted or which bears one or two substituents selected from halogen, trifluoromethyl, hydroxy, amino, nitro, carbamoyl and cyano, and alkyl, alkenyl, alkoxy, alkenyloxy, alkylthio, alkanoyl, carbamoylalkyl and alkanoylamino each of up to 6 carbon atoms, or Ar is 4- or 5-indanyl, 5- or 6-(1,2,3,4-tetrahydronaphthyl) or 2,3-dihydroxy-1,2,3,4-tetrahydronaphth-5-yl;

wherein $R^1$ is halogen, cyano, trifluoromethyl or trifluoromethylthio;

wherein either $R^2$ and $R^3$, which may be the same or different, each is hydrogen or alkyl of up to 6 carbon atoms; or $R^2$ is hydrogen and $R^3$ is cycloalkyl of 3 to 6 carbon atoms or cycloalkyl-alkyl wherein cycloalkyl is of 3 to 6 carbon atoms and alkyl is of up to 6 carbon atoms;

wherein $R^4$ is hydrogen and $R^5$ is hydrogen or alkyl of up to 6 carbon atoms;

wherein $R^6$ and $R^7$, which may be the same or different, each is hydrogen or alkyl of up to 6 carbon atoms;

and wherein A is alkylene of 2 to 6 carbon atoms; or an acid-addition salt thereof.

2. A compound as claimed in claim 1 wherein Ar has the meaning stated in claim 1, wherein $R^1$ is chloro, wherein $R^2$, $R^3$, $R^4$, $R^5$, $R^6$ and $R^7$ are all hydrogen and wherein Ar is ethylene or 1,1-dimethylethylene, or an acid-addition salt thereof.

3. An alkanolamine derivative as claimed in claim 2 wherein Ar is α-naphthyl, or phenyl which is unsubstituted or which bears a single substituent in the 2-position which is a fluoro, chloro, nitro, cyano, methyl, ethyl, allyl or methoxy substituent, or an acid-addition salt thereof.

4. An alkanolamine derivative as claimed in claim 1 wherein Ar is α- or β-naphthyl, or phenyl which is unsubstituted or which bears one or two halogen, alkyl, alkenyl or alkoxy substituents, wherein $R^1$ is chloro, wherein $R^2$, $R^3$, $R^4$, $R^5$, $R^6$ and $R^7$ are all hydrogen and wherein A is as defined in claim 1 but also is such that no more than 2 carbon atoms separate the two nitrogen atoms.

5. The compound:

N-β-(2-hydroxy-3-α-naphthyloxypropylamino)ethyl-(3,5-diamino-6-chloropyrazine-2-carbox)amide;

N-β-(2-hydroxy-3-phenoxypropylamino)ethyl-(3,5-diamino-6-chloropyrazine-2-carbox)amide;

N-β-(2-hydroxy-3-o-fluorophenoxypropylamino)ethyl-(3,5-diamino-6-chloropyrazine-2-carbox)amide; or N-[2-methyl-2-(2-hydroxy-3-o-tolyloxypropylamino)-propyl]-(3,5-diamino-6-chloropyrazine-2-carbox)amide, or an acid-addition salt thereof.

6. A pharmaceutical composition suitable for use in treating heart disease or hypertension, comprising as active ingredient at least one compound, or an acid-addition salt thereof, claimed in claim 1, in association with a pharmaceutically-acceptable diluent or carrier therefor.

7. A composition as claimed in claim 6 which also contains one or more drugs selected from sedatives, vasodilators, other diuretics, hypotensive agents, cardiac membrane stabilising agents, agents used in the treatment of Parkinson's disease and other tremors, cardiotonic agents, and α-adrenergic blocking agents.

8. A method for the treatment of heart disease or hypertension in a warm-blooded animal which comprises administering to said animal an effective amount of at least one compound claimed in claim 1.

9. A compound according to claim 1, said compound being N-β-(2-hydroxy-3-α-naphthyloxypropylamino)ethyl-(3,5-diamino-6-chloropyrazine-2-carbox)amide.

* * * * *